United States Patent
Nicholls

(10) Patent No.: US 9,910,028 B2
(45) Date of Patent: Mar. 6, 2018

(54) POINT OF CARE SEPSIS ASSAY DEVICE AND METHOD

(71) Applicant: Anthony Nicholls, Liverpool (GB)

(72) Inventor: Anthony Nicholls, Liverpool (GB)

(73) Assignee: Sepsis Limited, Liverpool (GB)

(*) Notice: Subject to any disclaimer, the term of this patent is extended or adjusted under 35 U.S.C. 154(b) by 218 days.

(21) Appl. No.: 14/654,006

(22) PCT Filed: Dec. 20, 2013

(86) PCT No.: PCT/GB2013/053395
§ 371 (c)(1),
(2) Date: Jun. 19, 2015

(87) PCT Pub. No.: WO2014/096856
PCT Pub. Date: Jun. 26, 2014

(65) Prior Publication Data
US 2015/0346189 A1   Dec. 3, 2015

(30) Foreign Application Priority Data
Dec. 20, 2012 (GB) .................................. 1223079.3

(51) Int. Cl.
G01N 33/49 (2006.01)
G01N 21/59 (2006.01)
G01N 15/06 (2006.01)

(52) U.S. Cl.
CPC ............. *G01N 33/49* (2013.01); *G01N 15/06* (2013.01); *G01N 21/59* (2013.01); *G01N 33/491* (2013.01); *G01N 2015/0687* (2013.01)

(58) Field of Classification Search
None
See application file for complete search history.

(56) References Cited

U.S. PATENT DOCUMENTS

| 7,355,194 B2* | 4/2008 | Tobimatsu ............. G01N 21/51 250/573 |
| 2006/0147998 A1* | 7/2006 | Jones .................. G01N 33/6893 435/7.1 |
| 2011/0306120 A1* | 12/2011 | Nicholls ............. B01F 13/0071 435/287.2 |
| 2012/0220047 A1* | 8/2012 | Seifried ............ B01L 3/502753 436/178 |

FOREIGN PATENT DOCUMENTS

| KR | 20110091106 | 8/2011 |
| WO | 200136666 | 5/2001 |
| WO | 200196864 | 12/2001 |
| WO | 2006060386 | 6/2006 |
| WO | 2007025559 | 3/2007 |
| WO | 2010007432 | 1/2010 |

OTHER PUBLICATIONS

Baldini et al., "Point of care optical device for sepsis diagnosis", Proceedings of the SPIE—The International Society for Optical Engineering SPIE, 2009, 7503.
Toh et al., "Biphasic transmittance waveform in the APTT coagulation assay is due to the formation of a Ca(++)-dependent complex of C-reactive protein with very-low-density lipoprotein and is a novel marker of impending disseminated intravascular coagulation", Blood, 2002, 100:2522-2529.
United Kingdom Intellectual Property Office (UKIPO), Application No. GB1223079.3, Search Report, dated 2013.

* cited by examiner

*Primary Examiner* — Robert Yamasaki
(74) *Attorney, Agent, or Firm* — Klauber & Jackson LLC

(57) ABSTRACT

Disclosed is a point of care sepsis assay comprising a disposable assay cartridge with a sample inlet for a blood sample, a filter to isolate blood plasma, a source of multivalent cations to cause a turbidity change in the plasma sample and a transparent window to measure the change in turbidity and the use of said assay in the diagnosis of sepsis.

18 Claims, 3 Drawing Sheets

POINT OF CARE SEPSIS ASSAY DEVICE AND METHOD

CROSS REFERENCE TO RELATED APPLICATIONS

Figure 1:
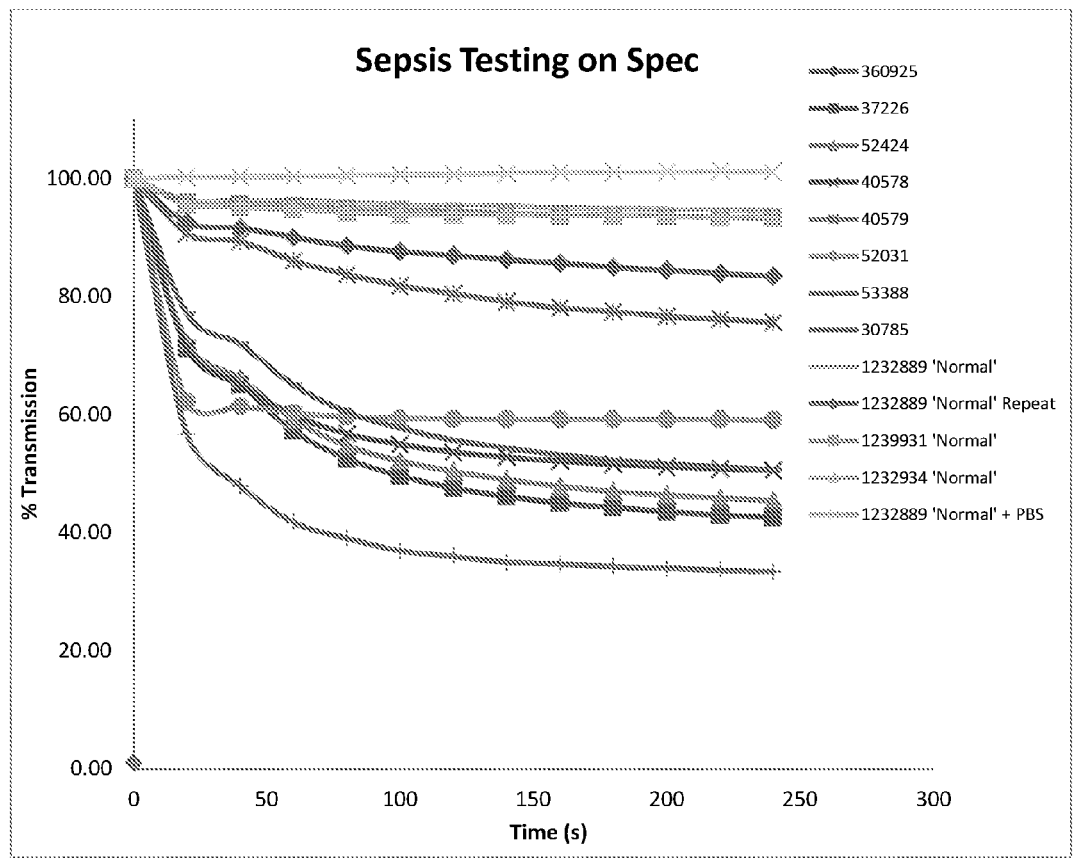

The present application is a National Stage Application which claims priority under 35 U.S.C. § 120 from copending PCT Application No. PCT/GB2013/053395, filed Dec. 20, 2013, which in turn claims priority from Great Britain Application No. 1223079.3, filed Dec. 20, 2012. Applicant claims the benefits of 35 U.S.C. § 120 as to the PCT application and priority under 35 U.S.C. § 119 as to the said Great Britain application, and the entire disclosures of both applications are incorporated herein by reference in their entireties.

FIELD OF THE INVENTION

The present invention relates generally to the field of disposable assay test devices, particularly for use in point-of-care assays. The invention further relates to the use of such devices, including kits comprising such devices, to facilitate the accurate measurement of the levels of sepsis in the blood.

BACKGROUND

Sepsis, or blood poisoning, is a potentially deadly medical condition characterized by a whole-body inflammatory state triggered by an infection. Sepsis is a vast clinical entity that takes many forms. The pathophysiology of a host response to infection is complex and the signs and symptoms of systemic inflammation may have an infectious or non-infectious etiology and are not specific. In response to microbes or viruses in the blood, urine, lungs, skin, or other tissues, the body may develop a systemic inflammatory response, eventually resulting in organ dysfunction and death. Patients with systemic infection are often difficult to distinguish from patients with similar clinical signs and laboratory findings without infection. Infection has multiple causes including that caused by bacterium, fungi, parasites and viruses.

Sepsis can be identified by the presence of pathogenic organisms in the bloodstream. Sepsis is usually treated with intravenous fluids and antibiotics. Sepsis can be the result of the presence of more than one type of organism, and there it is important to both identify the presence of the infection as early as possible before severe symptoms occur, and to regularly monitor blood samples from the patient during treatment to ensure the antibiotics are effective and the patient does not suffer from further infections.

Bacteriological evidence of infection may not develop at the same time as clinical signs of distress. Further, it requires time to grow a culture of organism from a blood sample to confirm the presence of infective bacteria and the results may be incorrect due to contamination, etc. As used herein, severe infection may include a diagnosis of sepsis, severe sepsis, septicaemia, and septic shock as well as disseminated intravascular coagulation ("DIC"). Also included in the definition of infection is systemic inflammatory response syndrome "SIRS" although it may have infectious as well as non-infectious origin (both of which are encompassed herein). SIRS may exhibit or develop into systemic inflammation that ultimately leads to multiple organ dysfunction syndrome. Patients with SIRS may develop the syndrome from infection, trauma, burns, pancreatitis, etc.

As used herein hemostatic dysfunction may be defined as an error in coagulation. For both DIC and sepsis, there is increasing recognition of common and overlapping pathophysiological pathways that link inflammation and coagulation. The recent therapeutic success of recombinant human activated protein C (APC) in severe sepsis especially after a myriad of unsuccessful strategies would support this further. APC suppresses thrombin generation via the inactivation of coagulation co-factors, Va and VIIIa and is also thought to have anti-inflammatory properties.

There is a continuing need to find early indicators or markers of infection, SIRS and hemostatic dysfunction due to lack of specificity of current methods of diagnosis. An early diagnosis may greatly increase recovery of the patient and reduce the morbidity and mortality rates associated with this population. Further a diagnostic marker or test to monitor the efficacy of treatment of the host response to infection, SIRS and hemostatic dysfunction is needed as well.

The time dependent measurement profiles of coagulation screening assays have been associated with predicting congenital, acquired imbalances and hemostatic dysfunction as described in Givens et al. WO 96/41291 and Toh et al. WO 00/46603. Once such profile is that of an activated partial thromboplastin time ("APTT") assay having a decrease in plasma light transmittance before clot formation, now commonly referred to as a biphasic waveform (also referred to herein as BPW). This BPW has been associated with critically ill patients having DIC which is common in many primary diseases including sepsis. The biphasic waveform on coagulation instruments offers a simple and rapid test for early diagnosis of hemostatic dysfunction, including DIC.

As described in WO 01/96864 (Dec. 20, 2001), a calcium-dependent complex between C reactive protein (CRP) and lipoprotein (particularly very low density lipoprotein (VLDL)) has been identified as the molecular mechanism underlying the biphasic waveform. The complex may be used to identify patients with sepsis, SIRS and septicaemia in addition to patients with other hemostatic dysfunction that can lead to bleeding or thrombosis including DIC. Further, WO 01/96864 describes detecting the complex by a clotting assay, latex agglutination or gold sol assay, and immunoassay whereby the precipitate is formed prior to or in the absence of clot formation, depending on the reagent used.

While the biphasic waveform and the CRP-lipoprotein complex provide advances in the early diagnosis of different kinds of severe infection and haemostatic dysfunction (including DIC and sepsis), there is a continued need to simplify the assays further, and therefore a simple point of care version of the assay which can be carried out using a small amount of blood and gives an immediate read out is highly desirable.

SUMMARY OF THE INVENTION

Disclosed is a point of care sepsis assay comprising a disposable assay cartridge with a sample inlet for a blood sample, a filter to isolate blood plasma, a source of multivalent cations to cause a turbidity change in the plasma sample in the presence of sepsis and a transparent window to measure the change in turbidity. The multivalent cations may be divalent cations. The divalent cations may be calcium. The cations may be dried onto the surface of the device cartridge. The invention also includes a reader device instrument for measuring the turbidity change in the sample. The reader instrument is configured to hold the device cartridge in a beam of visible light and to measure the transmittance of the sample over time. The device may be used to measure sepsis.

FIGURES

Figure 2:
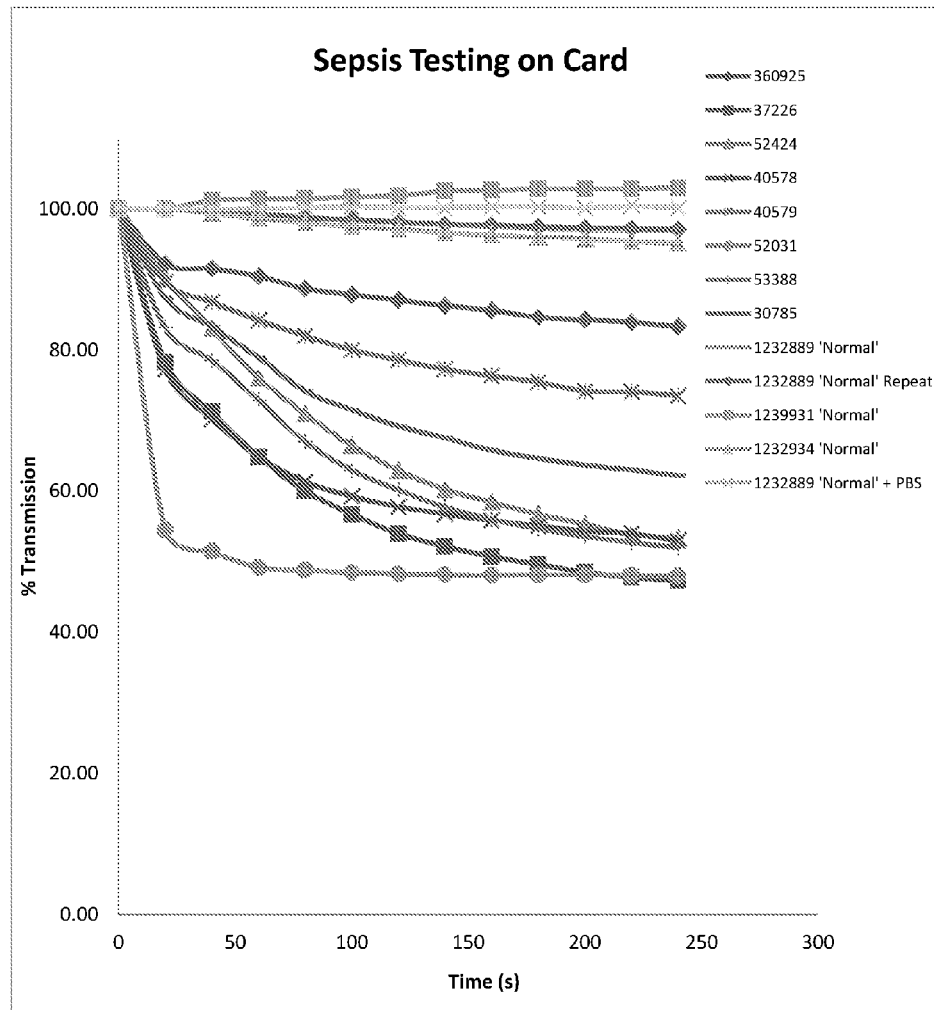
Figure 3:
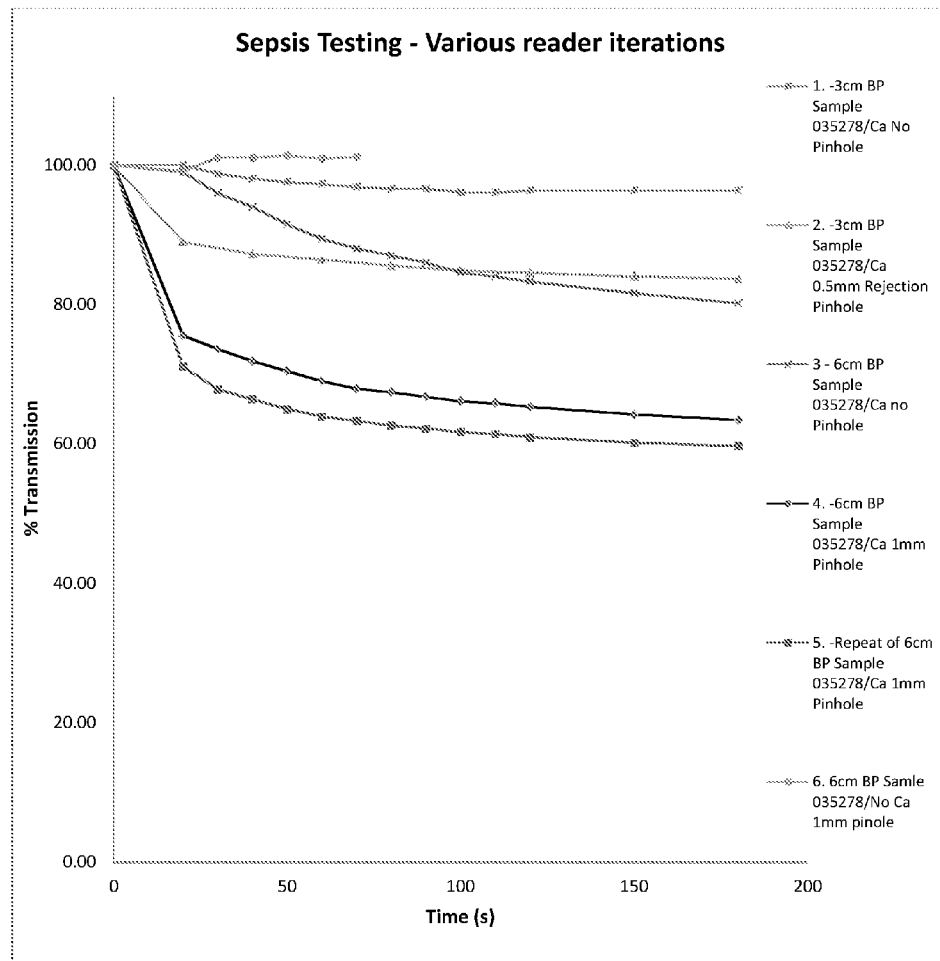

FIG. 1 shows the results of testing sepsis and control samples using a conventional spectrophotometer.
FIG. 2 shows the results the same sepsis and control samples on a card device of the invention.
FIG. 3 shows a graphical plot of the data shown in tables 1 and 2

DESCRIPTION

Disclosed is a point of care sepsis assay method comprising a disposable assay cartridge with a sample inlet for a blood sample, a filter to isolate blood plasma, a source of multivalent cations, to cause a turbidity change in the plasma sample in the presence of sepsis and a transparent window to measure the change in turbidity. The multivalent cations may be trivalent cations or divalent cations. The divalent cations may be calcium. The cations may be dried onto the surface of the device cartridge such that they are resuspended by addition of the blood plasma. The invention also includes a reader device instrument for measuring the turbidity change in the sample. The reader instrument is configured to hold the device cartridge in a beam of visible light and to measure the transmittance of the sample over time. The assay is performed relative to a control where the cations are absent, which in the point of care device may be carried out on the same device, either in a second separate reaction chamber, or in a separate portion of the same reaction chamber. The device may be a single use cartridge which is discarded after a single sample has been measured.

An existing assay for sepsis measures the change in turbidity of blood plasma induced by divalent metal ions. The assay can be carried out in a microtitre plate. The existing test uses calcium chloride and measures the loss of transmission of light by the sample over time. Patient with sepsis induce rapid precipitation in the presence of calcium, and hence a decrease in light transmission due to the increase in turbidity. In patients without sepsis, the solution stays clear and the transmission is unchanged. The transmittance can be monitored at any wavelength in the visible spectrum, for example 405-580 nm. The precipitation/turbidity increase occurs rapidly, and can be measured with 30-60 seconds.

An aspect of the present invention is that the divalent cations can be dried onto the surface of the microtitre plate, and resuspended by addition of the undiluted plasma sample. This dried cation source can also be applied to a reaction chamber or channel of a point of care device. The window of cation concentration may be greater than 10 mM, for example 10-100 mM The cations may be metal ions, for example calcium ions. Where concentrations are stated, the concentration referred to is the concentration of the rehydrated sample for which the transmittance/turbidity is being measured.

The point of care device requires that the sample be applied as whole blood, and therefore then device must be capable of containing a means such as filter to remove cellular material and ensure that only plasma enters the reaction chamber. The device may be adapted with an inlet that may be attached to a suitable filter, for example a luer inlet suitable for a syringe. The filter may be attached to a syringe rather than the device itself such that the filter can be removed prior to the device entering the reader to be read. The invention therefore requires the cartridge to have a connection suitable for a filter or other method of isolating blood plasma from whole blood, but the filter does not have to be physically integral to the device. Whole blood must be applied to the device, and the device must contain a means for obtaining blood plasma, and hence the device must either contain a filter or have a means whereby a blood sample can be turned into blood plasma using a filter which can be directly attached and removed. The filter must be attached at the point the blood sample is applied to the device, but can be removed once the blood sample has been applied. The filter can be integral to the device such that its removal is not possible.

The blood sample may be applied as undiluted whole blood, or may be treated, for example with citrate ions, in order to prevent precipitation occurring prior to addition to the assay device. After application of the blood to the device, the sample is processed without further dilution. The blood sample can be obtained, for example as a finger prick, which can be applied directly to the device, or can be obtained as a blood draw into syringe. If the blood is drawn into a syringe, the filtration to obtain plasma can be carried out as the sample enters the device.

The filter may be formed of a fibrous matrix to retard movement of, for example, red blood cells. Suitable materials include foams, glass fibres (such as borosilicate), sol-gel filters, chromatographic media such as filter papers or membranes such as nitrocellulose, polysulfone or polyester. In some embodiments, the filter may comprise reagents, for example, binding agents such as antibodies or beads which bind to and remove unwanted components from an aqueous sample. The filter may also comprise one or more pre-treatments, precipitating agents, surfactants/detergents, assay reagents, dyes, blocking agents or ligand binding inhibitors. Blocking agents and ligand binding inhibitors may limit the interference of particular components of the aqueous sample, for example Human Serum Albumin (HSA), with the assay. Thus, the filter may comprise an HSA extraction means such as anti-HSA antibodies for example, or any other means that uses for example precipitation, immobilisation and the like.

The device must contain a pre-loaded source of multivalent cations, such as divalent cations. Pre-loaded means the cations must be present in the device before the blood plasma sample is introduced. The cations may be present in one or more reactions chambers. The cations may be present in wet or dry form. The cations may be present in only a portion of the device, which may have more than one reaction chamber. The cations may be present in one chamber of a device with more than one chamber, for example the device may have two reaction chambers, one of which contains calcium. The two or more chambers may radiate from a central sample inlet region where the sample is introduced to the assay device. The filter may be located in the central region, or the sample may have been filtered prior to entering the sample inlet. If the cations are in dried form, only a portion of the reaction chamber may contain the cations, and thus both the reaction and control can be measured in one chamber. In all instances where cations are referred to, the cations may be metal ions, including calcium or magnesium. The window of cation concentration may be greater than 10 mM, for example 10-100 mM.

Use of the term 'dry form' refers to components that are maintained in a form in which they are generally substantially free from, or depleted of, liquid or moisture; that is they are not in solution until reconstituted by the performance of the assay itself, rather than being reconstituted prior to and separate from the assay procedures. Thus, the aqueous sample itself reconstitutes the dry reagent or reagents, thereby eliminating the need for separate reconstitution buffers and steps.

The reaction chamber of the device may comprise a closed channel. The reaction chamber may be a flow channel. The reaction chamber may have a defined volume. The volume of the reaction chamber may be for example 10-50 microliters (μL). The dimensions of the channel may be for example 0.5 mm-2 mm in height and depth, and 1-3 cm in length. The dimensions of the channel may be for approximately 1.5 mm in height, 1.5 mm in depth, and 2 cm in length.

The reaction chamber or channel may comprise an amphipathic polymer. Amphipathic polymers may be used to promote fluid flow and/or mixing of aqueous solutions, for example with 'dry' components combined within or as layers above or below a coating of an amphipathic polymer. The use of amphipathic polymers also has the advantage that lateral flow of fluids is improved, for example, over the traditional 'wicking' with porous materials such as is disclosed in U.S. Pat. No. 6,485,982. Wicking methods of the prior art rely on the use of a support vehicle such as paper or a membrane through which liquid is drawn by capillary action. The use of amphipathic polymers removes the need for a support vehicle, such as a membrane, with the effect that liquids may travel greater distances or at greater speeds along, for example, microtubes, surfaces, hydrophobic surfaces and the like than by capillary action alone. Thus, through use of an amphipathic polymer the capillary flow rate is increased and/or the fluid flows/travels greater distances than would be expected by capillary action alone.

An amphipathic polymer may be used to coat a fluid flow pathway. Alternatively the amphipathic polymer may be in the form of a coating or film on the surface of the flow pathway or may be in the form of a powder, pellets, microparticles, nanoparticles, picoparticles or filling within a void or cavity of the flow path. Where the amphipathic polymer is a filling within a cavity it may fill the cavity entirely or may be a partial filling with, for example, gaps. The amphipathic polymer may form the flow pathway, for example, as a track or path on a hydrophobic surface along which fluid flow can occur. For example, the amphipathic polymer may be printed (such as by inkjet or bubble-jet printing), painted, sprayed or applied onto a surface, such as a flat surface, for example to form 'tracks' and/or layers. Reagents may be combined, such as by mixing, with the amphipathic polymer or may be arranged as layers above, below or beside the amphipathic polymer.

Polyethylene glycol (PEG) is an amphipathic polymer. Useful molecular weights of PEG include from about 600 to 10,000 Da, and between about 1000 to 3000 Da. Polyethylene glycol, also known as polyethylene oxide (PEO) or polyoxyethylene (POE)), is an oligomer or polymer of ethylene oxide. PEGs are available over a wide range of molecular weights from 300 g/mol to 10,000,000 g/mol. PEG has the following general structure:

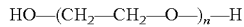

Numbers are frequently included in the names of PEGs to indicate their average molecular weights. For example, a PEG with n=80 would have an average molecular weight of approximately 3500 daltons and would be labelled PEG 3500.

Generally PEGs include molecules with a distribution of molecular weights. Whilst PEGs having different molecular weights find use in a variety of applications due to their differing physical properties, such as viscosity, their chemical properties are nearly identical. Different forms of PEG are also available dependent on the initiator used for the polymerization process, such as monofunctional methyl ether PEG (methoxypoly(ethylene glycol)), abbreviated mPEG. PEGs are also available with different geometries. Branched PEGs have 3 to 10 PEG chains emanating from a central core group. Star PEGs have 10-100 PEG chains emanating from a central core group. Comb PEGs have multiple PEG chains normally grafted to a polymer backbone. PEGs may also be covalently coupled to other molecules in a process known as PEGylation which may be advantageous when using the fluid flow properties of PEG for reagent mixing for example.

A further example of an amphipathic polymer is an amphipathic polypeptide, that is, a polypeptide which has a secondary structure such that the polypeptide has both a hydrophilic and a hydrophobic face. Other amphipathic polymers include polyvinyl alcohol (PVA) and ionic polymers.

The channel may contain a source of dried cations along part of its length. The cations may be in the part of the channel furthest from the sample inlet.

The cations may be supplied in the form of multivalent organic compounds. The organic compounds may be polymers, for example polylysine. The organic compounds may be dried onto the surface of the device.

Where the cations are metal ions, the cations may be dried into the surface of the device with polymeric reagents to aid dispersion, stability and resuspension. The polymeric reagents may be polyethylene glycols, for example methyl polyethylene glycol. Alternatively the metal ions may be microencapsulated. The cations must be dried in a form that allows rapid resuspension upon addition of the plasma sample.

The reaction chamber of the cartridge must comprise a viewing window with is transparent to visible light. The window may be transparent at 480 nm. The optical path length of the transparent window may be 0.5 mm to 10 mm. The optical path length of the transparent window may be 0.5 mm to 2 mm. The optical path length may be 1 mm or 1.5 mm.

The device may be made of plastic or glass. The transparent window may be made of transparent plastic. The dried reagents may be pre-absorbed onto one of the surfaces, and the device then assembled to incorporate the dried reagents and form a defined reaction chamber. For example the dried reagents may be prepared in tape form, and the tape used to seal an open channel to form a closed reaction chamber of defined volume.

The reaction chamber may be of a size that the plasma sample is drawn in by capillary action. Alternatively the chamber may be sealed under negative atmospheric pressure such that the sample is drawn in by suction. The reaction chamber may have an outlet to allow air to escape as the fluid enters.

Reader Device

The cartridge device containing the reaction can be measured on a reader device. The reader device should be capable of holding the reaction cartridge, and contain a source of visible light. The wavelength of the light source may be between 405-580 nm, for example 480 nm. The source of the light may be a bulb, laser or light emitting diode (LED). The reader may comprise an excitation filter to select the excitation wavelength. The reader may contain a measuring element for detecting the transmission through the sample. The reader may contain a pinhole to minimise the amount of light reaching the measuring element. The measuring element may be a photodiode.

The housing of the assay reader is usually adapted to enable it to be placed in functional communication with an assay cartridge. For example, the assay cartridge device may be inserted into, placed on or attached to the reader and the reader may comprise docking means, such as a slot, or alignment means to enable the assay device to be inserted, placed or attached appropriately.

The pinhole may be for example 3 mm in diameter. The pinhole may be less than 3 mm in diameter. The pinhole may be 0.5-1 mm in diameter. The pinhole may be 0.5, 0.8 or 1 mm in diameter.

The sample may be held between 1-10 cm from the photodiode to be measured. The sample may be held 3-6 cm from the photodiode to be measured.

The reader can be capable of recording the transmittance continually, or at defined time points. The reader can also include analytical software to plot a recording of the transmittance over a period of time, say 120 seconds. The reader may take measurements at defined timepoints. The reader may take measurements at three or more defined timepoints, for example 10, 30 and 60 seconds. The reader can be configured such that no user input is required in order to generate a test result.

Method of Use

Included herein is the use of a point of care assay for blood sepsis. The use involves a method of detecting sepsis comprising the steps of;
 a) obtaining a sample of whole blood;
 b) adding the blood sample to a point of care device comprising a filter to obtain blood plasma and a source of multivalent cations;
 c) measuring the change in turbidity of the blood plasma; and
 d) correlating a lowering of the light transmission with the presence of sepsis.

The point of care device may have any of the features described above. The measurement may be taken on a reader instrument as defined above.

Kits

In another aspect of the invention there is provided a kit comprising a package of components for performing a sepsis assay.

The kit may comprise one or more of a number of components such as (i) a means for sterilising a patient's skin prior to taking a blood sample, for example by a finger prick sample or via a syringe draw. Conventional means is a piece of fabric or gauze which includes a sterilant such as an alcohol, or antibacterial agent such as bisbiguanides, for example chlorhexidine as a soluble salt in aqueous or alcoholic solution; (ii) skin penetrating means such as a conventional lancet device preferably comprising a safety sleeve. Alternatively the needle may be part of a conventional syringe assembly including barrel and plunger; (iii) an assay device according to the first aspect of the invention; (iv) gauze or adhesive plasters to cover the skin puncture wound; (v) instructional leaflets providing details on use of the device (vi) disposable gloves to avoid blood contact; (vii) an assay reader.

TEST DATA AND EXAMPLES

1. Assay Performed on a Phillips PU8730 Spectrophotometer:
 A spectrophotometer cell that had a pathlength of 1.5 mm was used to test the assay. The absorbance was set to 480 nm. For the blank reading, 2 µl of PBS was added to a biphasic plasma sample (18 µl). This mixture was mixed well and added to the cell (20 µl). The door was then closed and readings were taken every 10 seconds up to 4 minutes. The cell was then washed with PBS and allowed to dry. This process was repeated with the PBS being substituted for 100 mM $CaCl_2$ (2 µl).
 This entire procedure was repeated for each of the tested plasma samples.
2. Assay Performed on the Prototype Device Platform with Reaction Channel:

A clear reaction chamber was constructed to effectively monitor the sepsis turbidity assay. In order to achieve a prototype card two pieces of topaz plastic were used with the inclusion of clear films provided by Cadillac Plastic Limited (8010MC.175). One piece was cut in half and a 1 mm channel (ca. 1 mm optical pathlength) was created along the length of the card. This was then sectioned off with black masking tape to allow light to pass through the desired read area.

Sample Preparation:
Due to the assay requiring a blank reading to be taken (sample in buffer), the reaction chamber on card had to be washed out after blank testing. As the reaction takes place so quickly it is not possible to take a blank sample measurement and then add calcium to the chamber in situ. Thus samples are prepared as follows:

Blank Mixture:
5 µl of PBS buffer was added to 45 µl of biphasic plasma sample (sample ref 035278) (Samples were provided by Colin Downey—University of Liverpool). This reaction mixture was mixed and 20 µl was added to the prototype card. This was then read on a prototype reader taking regular readouts from a picoammeter (set to uA) over a 1 min period. This card was then removed, washed with PBS and allowed to dry.

Reaction Mixture:
5 µl of 100 mM $CaCl_2$ was added to 45 µl of the of biphasic plasma sample (035278). This mixture was again mixed quickly, before 20 µl was added to the card and read over a 3 minute period using the 'continuous mode' on the reader software. This card was then removed, washed with PBS and allowed to dry before testing again.

This entire procedure was repeated for 8 biphasic and 3 normal samples as follows:

The sample reference numbers used in this study were as follows:
Biphasic
360925 37226 52424 40578 40579 52031 53388 30785
Normal
1232889 1239931 1232934

FIG. 1 shows the samples measured on a conventional spectrophotometer. FIG. 2 shows the same samples measured on a prototype card device. Overall the data on the prototype device shows equivalence between the channel device and the spectrophotometer cell. The general trends between the two platforms seem to be consistent. Loss of signal is comparable with the exception of two samples 52031 & 53388. However, both methods would lead to the same clinical conclusion. There is a slightly greater loss of transmission in the spectrophotometer due to the increased pathlength, as it was at 1.5 mm rather than the 1 mm on the card.

Timing of the initial reaction pathway was again difficult due to 'offline' mixing of the sample before addition to either the card or the cell. This makes it extremely difficult to closely monitor the first 20-40 seconds of the reaction which are critical in seeing the loss in signal. It is also unclear why we see a loss and/or increase in signal of 'normal' samples. Although this is negligible in the overall scale of the reaction, it may be that the wash step of the card after use may be leaving trace calcium deposits in the chamber giving rise to a change in signal. This would not occur on single use disposable cards.

Optimising and testing reader parameters

The reaction card, blank sample and plasma sample preparation were carried out as indicated above.

Specification of the reader
A white light LED was used as the light source.
A 480 nM narrow band pass tophat filter was used to control the wavelength.

A diode was connected up to a picoammeter.
A stage containing the diode was then positioned to give a distance of 3 or 6 cm between the diode and sample.
A 0.5 mm rejection pinhole was added to the light path.
This configuration was then tested.
Results:

TABLE 1

Results from various stages of reader modification.

| | 0.8 mm Pathlength, 3 cm Sample to Detector Distance no Pinhole | | 0.8 mm Pathlength, 3 cm Sample to Detector Distance, 0.5 mm Rejection Pinhole | | 0.8 mm Pathlength, 6 cm Sample to Detector Distance, no Pinhole | |
|---|---|---|---|---|---|---|
| Time | BP Sample 035278, 100 mM CaCl2 | % Transmission | BP Sample 035278, 100 mM CaCl2 | % Transmission | BP Sample 035278, 100 mM CaCl2 | % Transmission |
| 0 | 4.110 | 100.00 | 0.584 | 100.00 | 1.000 | 100.00 |
| 20 | 4.110 | 100.00 | 0.520 | 88.98 | 0.990 | 99.00 |
| 30 | 4.059 | 98.76 | missed | | 0.960 | 96.00 |
| 40 | 4.030 | 98.05 | 0.510 | 87.27 | 0.940 | 94.00 |
| 50 | 4.010 | 97.57 | missed | | 0.915 | 91.50 |
| 60 | 3.999 | 97.30 | 0.505 | 86.41 | 0.894 | 89.40 |
| 70 | 3.980 | 96.84 | missed | | 0.880 | 88.00 |
| 80 | 3.970 | 96.59 | 0.500 | 85.56 | 0.870 | 87.00 |
| 90 | 3.970 | 96.59 | missed | | 0.860 | 86.00 |
| 100 | 3.950 | 96.11 | 0.496 | 84.87 | 0.846 | 84.60 |
| 110 | 3.950 | 96.11 | missed | | 0.840 | 84.00 |
| 120 | 3.960 | 96.35 | 0.494 | 84.53 | 0.833 | 83.30 |
| 150 | 3.960 | 96.35 | 0.491 | 84.02 | 0.816 | 81.60 |
| 180 | 3.960 | 96.35 | 0.489 | 83.68 | 0.802 | 80.20 |

The results show that the accuracy of the test on the reader is improved using the pinhole, and by increasing the distance between the sample and the measuring element (detector).

The assay was repeated to record two time profiles of the sample 035278 vs a sample without calcium at the optimised reader configuration (0.8 mm optical path length, 6 cm Sample to Detector Distance, 1 mm Rejection Pinhole):

TABLE 2

Results following final reader modification.

0.8 mm Pathlength, 6 cm Sample to Detector Distance, 1 mm Rejection Pinhole

| Time | BP Sample 035278, 100 mM CaCl2 | % Transmission | Repeat BP Sample 035278, 100 mM CaCl2 | % Transmission | Control BP Sample 032578 no Ca | % Transmission |
|---|---|---|---|---|---|---|
| 0 | 0.628 | 100.00 | 0.640 | 100.00 | 0.930 | 100.00 |
| 20 | 0.474 | 75.53 | 0.455 | 71.09 | 0.922 | 99.14 |
| 30 | 0.462 | 73.61 | 0.434 | 67.81 | 0.940 | 101.08 |
| 40 | 0.451 | 71.86 | 0.425 | 66.41 | 0.940 | 101.08 |
| 50 | 0.442 | 70.43 | 0.416 | 65.00 | 0.943 | 101.40 |
| 60 | 0.433 | 68.99 | 0.409 | 63.91 | 0.939 | 100.97 |
| 70 | 0.426 | 67.88 | 0.405 | 63.28 | 0.941 | 101.18 |
| 80 | 0.423 | 67.40 | 0.401 | 62.66 | | |
| 90 | 0.419 | 66.76 | 0.398 | 62.19 | | |
| 100 | 0.415 | 66.12 | 0.395 | 61.72 | | |
| 110 | 0.413 | 65.81 | 0.393 | 61.41 | | |
| 120 | 0.410 | 65.33 | 0.390 | 60.94 | | |
| 150 | 0.403 | 64.21 | 0.385 | 60.16 | | |
| 180 | 0.398 | 63.42 | 0.382 | 59.69 | | |

FIG. 3 shows a plot of the data shown in tables 1 and 2. The results show the various optimisation and modification steps that the reader has undergone in order to be able to monitor the Sepsis turbidity assay in a channel format. The biphasic plasma sample shows no loss of transmittance in the absence of calcium. From the graph it is clear that the addition of a rejection pinhole and an increase in the sample-detector distance has improved the resolution in the assay in this format.

The invention claimed is:

1. A method of detecting sepsis using a device comprising a disposable assay cartridge with a sample inlet for a blood sample, a filter to isolate blood plasma from the blood sample, a reaction chamber containing a dried material containing a source of multivalent cations where the dried material is present only on a portion of the surface of the reaction chamber, the multivalent cations causing a turbidity change in the plasma sample in the presence of sepsis, and a transparent window to measure the change in turbidity, the method comprising adding a blood sample to the device; measuring the change in turbidity of the blood plasma caused by the multivalent ions relative to a control reading taken in a separate portion of the same reaction chamber where the cations are absent; and correlating a lowering of the light transmission with the presence of sepsis.

2. A method according to claim 1 wherein the device is a disposable, single use device.

3. A method according to claim 1 wherein the multivalent cation is a divalent cation.

4. A method according to claim 3 wherein the divalent cations are metal ions.

5. A method according to claim 4 wherein the metal is calcium.

6. A method according to claim 1 wherein the device comprises a reaction chamber of defined volume.

7. A method according to claim 6 wherein the volume of the reaction chamber is 10-50 microliters (μL).

8. A method according to claim 1 wherein the window is transparent at 480 nm.

9. A method according to claim 1 wherein the optical path length of the transparent window is 0.5 mm to 10 mm.

10. A method according to claim 1 wherein the optical path length of the transparent window is 0.5 mm to 2 mm.

11. A method according to claim 1 wherein the device comprises a second reaction chamber which does not contain the source of divalent cations.

12. A method according to claim 1 wherein the divalent cations are present at a final concentration of greater than 10 mM in the reaction chamber when the blood plasma has been added.

13. A method according to claim 1 wherein the cations are dried in a layer of water soluble polymer.

14. A method according to claim 13 wherein the polymer is polyethylene glycol or methyl polyethylene glycol.

15. A method according to claim 1 wherein the device is measured using a reader instrument comprising a source of visible light.

16. A method according to claim 15 wherein the reader instrument comprises a measuring element for detecting the amount of light passing through the sample.

17. A method according to claim 16 wherein the measuring element is a photodiode.

18. A method according to claim 16 wherein the reader instrument comprises a pinhole between the measuring element and the sample.

* * * * *